US00PP34925P2

(12) United States Plant Patent
Star

(10) Patent No.: US PP34,925 P2
(45) Date of Patent: Jan. 17, 2023

(54) ***SANGUISORBA* PLANT NAMED 'SWEET DREAM'**

(50) Latin Name: *Sanguisorba officinalis*
Varietal Denomination: Sweet Dream

(71) Applicant: Jan Star, Rijnsburg (NL)

(72) Inventor: Jan Star, Rijnsburg (NL)

( * ) Notice: Subject to any disclaimer, the term of this patent is extended or adjusted under 35 U.S.C. 154(b) by 0 days.

(21) Appl. No.: 17/752,840

(22) Filed: May 24, 2022

(30) Foreign Application Priority Data

Nov. 1, 2021 (QZ) ..... PBR 20212734

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Penny J. Aguirre

(57) ABSTRACT

The new cultivar of *Sanguisorba* plant named 'Sweet Dream' that is characterized by its flowers that are pink in color, its flowers that are slightly pendulous, and its upright plant habit.

2 Drawing Sheets

Botanical classification: *Sanguisorba officinalis*.
Variety denomination: 'Sweet Dream'.

CROSS REFERENCE TO A RELATED APPLICATIONS

This application claims priority to European Community Plant Variety Office (CPVO) Plant Breeder's Rights Application No. 2021/2734 filed on Nov. 1, 2021, under 35 U.S.C. 119(f), the entire contents of which is incorporated by reference herein. This application is also related to U.S. Plant Patent Application filed for a plant derived from the same breeding program that is entitled *Sanguisorba* Plant Named 'Red Dream' (U.S. Plant Pat. No. 32,441) and *Sanguisorba* Plant Named 'Big Dream' (U.S. Plant Pat. No. 33,601). This application is co-pending with U.S. Plant Patent Applications filed for plants derived from the same breeding program that are entitled *Sanguisorba* Plant Named 'Fall Dream' (U.S. Plant patent application Ser. No. 17/752,837), *Sanguisorba* Plant Named 'Tough Dream' (U.S. Plant patent application Ser. No. 17/752,844).

BACKGROUND OF THE INVENTION

The present invention relates to a new and distinct cultivar of *Sanguisorba officinalis* and will be referred to hereafter by its cultivar name, 'Sweet Dream'. 'Sweet Dream' represents a new Burnet, an herbaceous perennial grown for landscape use.

The inventor discovered the new cultivar, 'Sweet Dream', as a chance seedling in a trial garden in September of 2018 in Rijnsburg, The Netherlands. The parentage is unknown.

Asexual propagation of the new cultivar was first accomplished by division in 2018 by the inventor in Rijnsburg, The Netherlands. Asexual propagation by division has determined that the new cultivar is stable and reproduced true to type in successive generations.

SUMMARY OF THE INVENTION

The following traits have been repeatedly observed and represent the characteristics of the new cultivar. These attributes in combination distinguish 'Sweet Dream' as a unique cultivar of *Sanguisorba*.

1. 'Sweet Dream' exhibits flowers that are pink in color.
2. 'Sweet Dream' exhibits flowers that are slightly pendulous.
3. 'Sweet Dream' exhibits an upright plant habit.

'Sweet Dream' can be most closely compared to *Sanguisorba officinalis* cultivars 'Big Dream', 'Red Dream', 'Fall Dream', and 'Tough Dream'. 'Big Dream', 'Red Dream', 'Fall Dream', and 'Tough Dream' are all similar to 'Sweet Dream' in having upright plant habits and tall plant heights. 'Big Dream' differs from 'Sweet Dream' in having inflorescences and stamen filaments that are grey-purple in color. 'Red Dream' differs from 'Sweet Dream' in having a smaller plant size and flowers that are red in color. 'Fall Dream' differs from 'Sweet Dream' in having larger inflorescences, weaker branches, and flowers that are red in color. 'Tough Dream' differs from 'Sweet Dream' in having flowers that are red in color.

BRIEF DESCRIPTION OF THE DRAWINGS

The accompanying color photographs illustrate the overall appearance and distinct characteristics of the new *Sanguisorba*. The photographs were taken of a one-year-old plant of the new cultivar as field grown outdoors in Rijnsburg, The Netherlands and placed in a container for the photographs.

The photograph in FIG. 1 illustrates the overall habit and appearance of 'Sweet Dream' in bloom.

Figure 1:
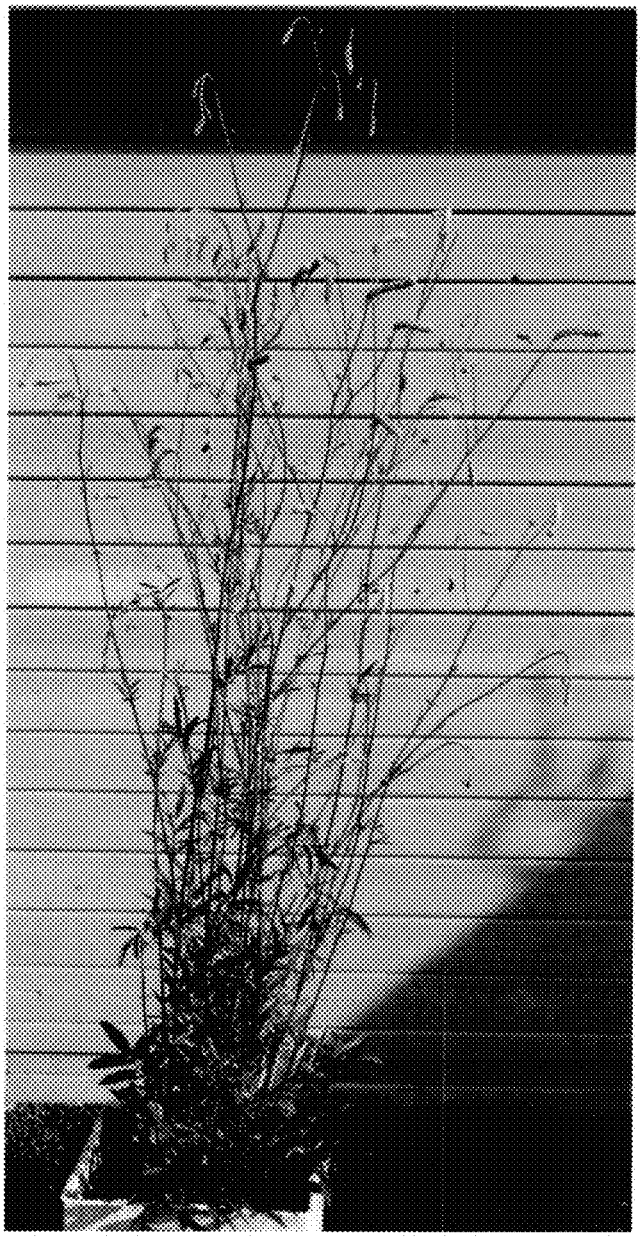
Figure 2:
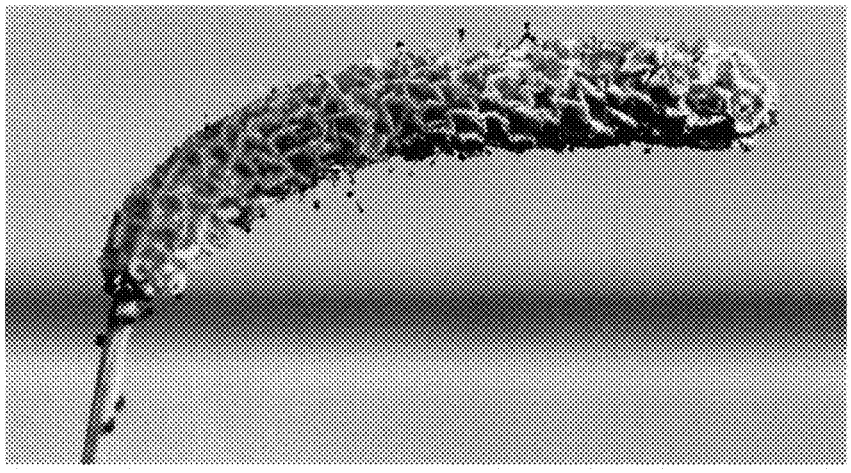

The photograph in FIG. 2 provides a close-up view of the inflorescences of 'Sweet Dream'.

Figure 3:
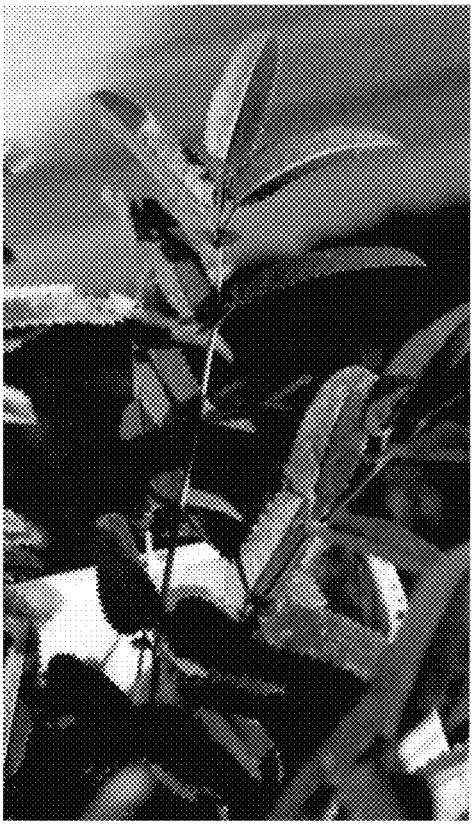

The photograph in FIG. 3 provides a close-up view of the foliage of 'Sweet Dream'.

The colors in the photographs are as close as possible with the photographic and printing technology utilized and color values cited in the detailed botanical description accurately describe the colors of the new *Sanguisorba*.

DETAILED BOTANICAL DESCRIPTION

The following is a detailed description of one-year-old plants from a division of the new cultivar as field grown in Rijnsburg, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—September in The Netherlands.

*Plant shape*.—Oblong, upright.

*Plant habit*.—Herbaceous perennial.

*Height and spread*.—Average of 1.35.5 m in height from soil level to top of foliar plane, 1.92 m in height from soil level to top of floral plane, 83.5 cm in spread.

*Hardiness*.—At least in U.S.D.A. Zones 4 to 9.

*Diseases and pests*.—No susceptibility or resistance to diseases or pests has been observed.

*Root description*.—Moderately fibrous, very freely branched, smooth, glabrous with no root hairs, main roots are an average of 3 mm in diameter, 164C in color.

*Propagation*.—Division.

*Growth rate*.—Vigorous.

Stem description:

*Shape*.—Round, moderately angled.

*Stem color*.—Young and mature; 144A.

*Stem size*.—Up to 133.2 cm in length and 6 mm in diameter.

*Stem aspect*.—Average of 15° to vertical (varying between 0° and 30°).

*Stem surface*.—Slightly glossy.

*Internode length*.—Up to 15.5 cm.

*Branching*.—Average of 13 main branches and 18 lateral branches per plant.

Foliage description:

*Leaf shape*.—Narrow obovate.

*Leaf division*.—Compound, imparipinnate; an average of 11 leaflets per leaf (ranges from 17 leaflets on the lower leaves to 5 leaflets on the upper leaves).

*Leaf base*.—Truncate.

*Leaf apex*.—Abruptly acute.

*Leaf aspect*.—Average of 30° to stem.

*Leaf arrangement*.—Alternate.

*Leaf size*.—Average of 35.4 cm in length (including petiole), 11.2 cm in width.

*Leaf attachment*.—Petiolate.

*Leaflet*.—Lanceolate to narrow oblong in shape, terminal leaflets; average of 6.6 cm in length, 1.7 cm in width, lateral leaflets; average of 6.4 cm in length and 1.7 cm in width, abruptly acute apex, truncate base.

*Leaflet venation*.—Pinnate, upper surface color 144A to 144B, lower surface 148C.

*Leaflet margins*.—Dentate to serrate.

*Leaflet surface*.—Both surfaces non-rugose, moderately glossy, matte.

*Leaflet color*.—Young upper surface 137B, young lower surface 138B, mature upper surface NN137B, mature lower surface a blend of 138B and 191A.

*Rachis (petiole) and petiolule*.—Rachis (petiole); average of 21.1 cm in length, 2.5 mm in diameter, petiolule; average of 2.3 cm in length and 1 mm in diameter, moderately glossy, smooth and glabrous, strong, upper surface color 143C, rachis tinged 187B at the leaflet nodes, lower surface 144B, petiolules slightly lighter 144B and 144C.

*Stipules*.—At the base of each leaf is a leafy stipule is present on each side, shaped falcate, average of 3.6 cm in length, 1.6 cm in width, both surfaces smooth and glabrous, margins dentate to serrate, top apiculate, upper side moderately glossy, color; NN137B, lower surface a blend of 138B and 191A, lower stem leaves; a leafy stipule is present on either side at the base of each petiolule, ovate in shape, average of 1.2 cm in length, average of 8 mm in width, both surfaces smooth and glabrous, margins dentate to serrate, both surfaces moderately glossy, color; NN137B, lower surface a blend of 138B and 191A.

Inflorescence description:

*Type*.—Terminal spikes of numerous, densely packed flowers in elongated ovoid to oblong shaped inflorescence, determinate.

*Inflorescence size*.—6.2 cm in height, 1.1 cm in diameter.

*Fragrance*.—Very faint and unpleasant.

*Flower lastingness*.—About 14 days, persistent.

*Flower quantity*.—Average of 225 flowers per spike, over 50,000 flowers and buds per plant.

*Flower aspect*.—Rotate, single, outward and freely flowering.

*Flower size*.—Average of 4 mm in height, diameter, and depth.

*Peduncle*.—Average of 18 cm in length, 1.75 mm in diameter, held in an average of 0°, secondary 40°, strong, smooth and glabrous, slightly glossy, 144A in color.

*Bud description*.—Average of 1.5 mm in length and diameter, globular in shape, smooth, glabrous, and matte surface, color; 157D, strongly tinged 187D, top 147A.

*Petals*.—Rotate, cruciform, average of 4, 1 row, unfused, 2 mm in length, 1.25 mm in width, broadly ovate in shape, tip is broadly acute and recurved, broadly cuneate base, entire margins, both surfaces glabrous, slightly velvety and matte, color; when opening and fully open upper surface; NN155B, when opening and fully open lower surface NN155B, tinged 75B, both surfaces fading to 59C.

*Calyx*.—Rotate, cruciform, average of 1 mm in length, 1.2 mm in diameter.

*Sepal*.—An average of 4 in 1 row, average of 1.5 mm in length and 0.75 mm in width, narrow ovate in shape, acute tip, cuneate base, entire margins, both surfaces smooth and glabrous, color; when opening and fully open upper and lower surface 150D.

*Flower bracts*.—None.

Reproductive organs:

*Gynoecium*.—Pistil: 1, average of 1 mm in length, stigma is flattened and club-shaped, 0.3 mm in length and 0.5 mm in diameter, 182C in color, style; average of 0.7 mm in length, N155C in color, ovary; 150D in color.

*Androecium*.—Stamens; average of 4, filament; 2.5 mm in length, N155B in color, anthers; short, kidney-shaped, 200A in color, 0.5 mm in length and width, pollen; low in quantity, 164B in color.

*Fruit/seed*.—None observed.

It is claimed:

1. A new and distinct cultivar of *Sanguisorba* plant named 'Sweet Dream' as herein illustrated and described.

* * * * *